United States Patent [19]

Shevlin et al.

[11] Patent Number: 5,628,754
[45] Date of Patent: May 13, 1997

[54] STENT DELIVERY GUIDE CATHETER

[75] Inventors: Michael R. Shevlin, La Mesa; James M. Shy, Chula Vista; William J. Boyle, Carlsbad; Paul W. Krejol, Poway, all of Calif.; Peter A. Lunn, Beverly, Mass.

[73] Assignee: Medtronic, Inc., Minneapolis, Minn.

[21] Appl. No.: 510,117

[22] Filed: Aug. 1, 1995

[51] Int. Cl.⁶ ..................................... A61F 11/00
[52] U.S. Cl. .................. 606/108; 606/192; 606/194; 606/195
[58] Field of Search ................... 606/108, 164, 606/170, 198, 194, 195; 128/772; 604/280, 96, 101, 28

[56] References Cited

U.S. PATENT DOCUMENTS

| | | | |
|---|---|---|---|
| 4,449,195 | 5/1984 | LeVecr et al. | 604/282 |
| 4,516,972 | 5/1985 | Samson | 604/282 |
| 4,733,665 | 3/1988 | Palmaz | 128/343 |
| 4,817,613 | 4/1989 | Jaraczewski et al. | 128/658 |
| 4,886,062 | 12/1989 | Wiktor | 128/343 |
| 4,898,591 | 2/1990 | Jang et al. | 604/282 |
| 4,932,959 | 6/1990 | Horzewski et al. | 604/96 |
| 4,960,410 | 10/1990 | Pinchuk | 606/194 |
| 5,123,917 | 6/1992 | Lee | 623/1 |
| 5,171,262 | 12/1992 | MacGregor . | |
| 5,192,297 | 3/1993 | Hull | 604/96 |
| 5,344,426 | 9/1994 | Lau et al. | 606/198 |
| 5,388,590 | 2/1995 | Horrigan et al. | 128/772 |
| 5,395,389 | 3/1995 | Patel | 606/194 |

FOREIGN PATENT DOCUMENTS

| | | |
|---|---|---|
| 0416734 | 3/1991 | European Pat. Off. . |
| 0630623 | 12/1994 | European Pat. Off. . |
| 0415332 | 1/1995 | European Pat. Off. . |

*Primary Examiner*—Robert A. Hafer
*Assistant Examiner*—Justine Yu
*Attorney, Agent, or Firm*—Michael R. Shevlin; Dianne M. F. Plunkett; Harold R. Patton

[57] ABSTRACT

The present invention is for a stent delivery guide catheter to be used in percutaneous transluminal coronary angioplasty (PTCA). The stent delivery guide catheter consists of a guide catheter body having proximal and distal ends with a cylindrical outer wall and a coaxial inner wall defining a inner lumen. A bladder is formed between the inner and outer walls and is in fluid communication with an inflation lumen. A radially expandable and compressible stent is located inside the guide catheter body and is removably attached to the inner wall in the area of the bladder. In use, a balloon catheter is slid inside the guide catheter with the balloon positioned under the stent. When the bladder is inflated, the stent is compressed radially inward and is deposited on the balloon catheter. The present invention can also be used without the stent to facilitate the exchange of an over-the-wire balloon catheter. The balloon catheter is pulled proximal to the inflatable bladder inside the guide catheter. The bladder is then inflated and compressed to hold the guidewire while the balloon catheter is exchanged.

25 Claims, 7 Drawing Sheets

STENT DELIVERY GUIDE CATHETER

FIELD OF THE INVENTION

The present invention relates to a guiding catheter used in Percutaneous Transluminal Coronary Angioplasty (PTCA) procedures. More particularly, the present invention concerns a guiding catheter having an inflatable bladder with a stent embedded in the wall of the guide catheter. When the bladder is inflated, the stent will be crimped and mounted onto a dilatation catheter balloon used for stent delivery.

BACKGROUND OF THE INVENTION

Dilatation balloon catheters are frequently used for the treatment of stenosis in the coronary arteries. This procedure is known as percutaneous transluminal coronary angioplasty (PTCA). According to this procedure, blockage in a coronary artery can be reduced by positioning a balloon dilatation catheter across the blockage and inflating the balloon, which causes stretching of the artery and pressing of the lesion into the artery wall to re-establish acceptable blood flow through the artery.

The procedure starts with the introduction of a guiding catheter into the cardiovascular system of a patient through the femoral artery in the groin area. The guide catheter is advanced through the arteries until its distal end is located near the desired coronary artery. Next a guidewire and balloon dilatation catheter are introduced into the guide catheter. The guidewire is first advanced out of the guiding catheter into the patient's coronary artery and is positioned across the stenosis. The dilatation catheter is then slid over the guidewire until the dilatation balloon is properly positioned across the stenosis. The balloon is then inflated to compress the stenosis and dilate the artery.

It is often desirable to do more than simply force a balloon against the stenosis or other restriction to compress any plaque in the artery wall and to open the lumen more fully. In many cases there may be restenosis of the artery, which may require another angioplasty procedure or a surgical bypass operation. To help prevent the artery from closing again, a physician can implant a stent inside the artery. A stent is a cylindrically shaped wire formed device intended to act as a permanent prosthesis. The stent is usually delivered to the artery in a compressed shape on a stent delivery catheter and expanded to a larger diameter once in place by a balloon.

In general, the typical procedure for implanting a stent includes first opening the artery with a balloon dilatation catheter procedure, as noted above. Once the artery is dilated, the balloon dilatation catheter is exchanged with another catheter carrying a stent. There are different methods used to exchange the balloon catheter with a stent delivery catheter. For an over-the-wire catheter, this involves exchanging the guidewire with an extension wire or extending the guidewire to allow catheter exchange. These methods can be difficult and time consuming.

Once the dilatation catheter is removed, the stent delivery catheter must be inserted. The stent delivery catheter is then advanced through the guide catheter to the stenosis and the stent is positioned to bridge the weakened portion of the artery. The balloon is then inflated and the stent is placed in the artery. Many patents disclose the construction and design of stents as well as the apparatus for positioning the stent in the artery. U.S. Pat. No. 4,733,665 to Palmaz discloses a number of stent configurations and a delivery catheter with the stent mounted on the inflatable portion of the catheter prior to insertion in the guide catheter. The stent is implanted by positioning it within the artery and monitoring its position on a viewing monitor. Once the stent is position as desired, the catheter is expanded and the stent is separated from the catheter body. The catheter is then withdrawn, leaving the stent in place in the artery. U.S. Pat. No. 4,886,062 to Wiktor, assigned to the same assignee as the present invention, discloses a stent carried on a dilatation balloon prior to insertion in the guide catheter and is positioned in the artery via a guiding catheter. The prior art does not allow loading the stent on the balloon of the dilatation catheter during the procedure without removing the catheter from the body or requiring a catheter exchange. This does not allow the physician the flexibility to use the same balloon catheter for dilatation and stent delivery or load the stent anytime during the procedure.

Guide catheters are known in the prior art. U.S. Pat. No. 4,516,972 to Samson shows a guiding catheter and method of manufacture having an inner liner made of slippery material, an intermediate layer of flexible material wound from ribbons to provide torsional rigidity and an outer jacket of flexible material all bonded together. U.S. Pat. No. 4,817,613 to Jaraczewski shows a guiding catheter and method of construction having a multiple layer construction with an inner flexible member surrounded by a pair of torque transmitting layers encased by an outer layer applied as a viscus material and cured to harden, joining the layers together.

Crimping stents on the end of dilatation balloons using a bladder technique is known in the prior art. European Patent Application Publication number 0630623A2 to Williams discloses a mechanism for stent loading on a catheter. The bladder described has an open end and a sealed end. A stent is loaded in the open end of the bladder, the collapsed balloon of a dilatation catheter is then inserted inside the stent. The bladder is then inflated to affix the stent to the balloon. The delivery catheter, now loaded with a stent, is ready to be inserted into the body of a patient for deployment. Williams device uses the bladder in a separate tool for loading stents onto balloon catheters prior to use.

Balloons and guide catheters are also known in the prior art. European Patent Application Publication number 0416734A1 to Coehlo, European Patent Application Publication number 0415332B1 to Keith, U.S. Pat. No. 5,395,389 to Patel, and U.S. Pat. No. 5,388,590 to Horrigan et al. have balloons with inflation lumens that are assembled in the guide catheter or are inserted into the guide catheter. When the balloons are inflated, the guidewire is trapped in place during a catheter exchange.

SUMMARY OF THE INVENTION

The object of the present invention is to provide a unique way of delivering a stent to the end of a balloon catheter that eliminates the need for catheter exchange. The present invention is for a stent delivery guide catheter to be used in percutaneous transluminal coronary angioplasty (PTCA). The stent delivery guide catheter consists of a guide catheter body having proximal and distal ends with a cylindrical outer wall and a coaxial inner wall defining an inner lumen. A bladder is formed between the inner and outer walls and is in fluid communication with an inflation lumen. A radially expandable and compressible stent is located inside the guide catheter body and is removably attached to the inner wall in the area of the bladder. In use, a balloon catheter is slid inside the guide catheter with the balloon positioned under the stent. When the bladder is inflated, the stent is compressed radially inward and is deposited on the balloon catheter. The present invention can also be used without the stent to facilitate the exchange of an over-the-wire balloon catheter. The balloon catheter is pulled proximal to the inflatable bladder inside the guide catheter. The bladder is then inflated and compressed to hold the guidewire while the balloon catheter is exchanged.

BRIEF DESCRIPTION OF THE DRAWINGS

The foregoing and other features of the present invention will be best appreciated with reference to the following detailed description of a specific embodiment of the invention, when read in conjunction with the accompanying drawings.

DETAILED DESCRIPTION OF THE PREFERRED EMBODIMENTS

Figure 1:
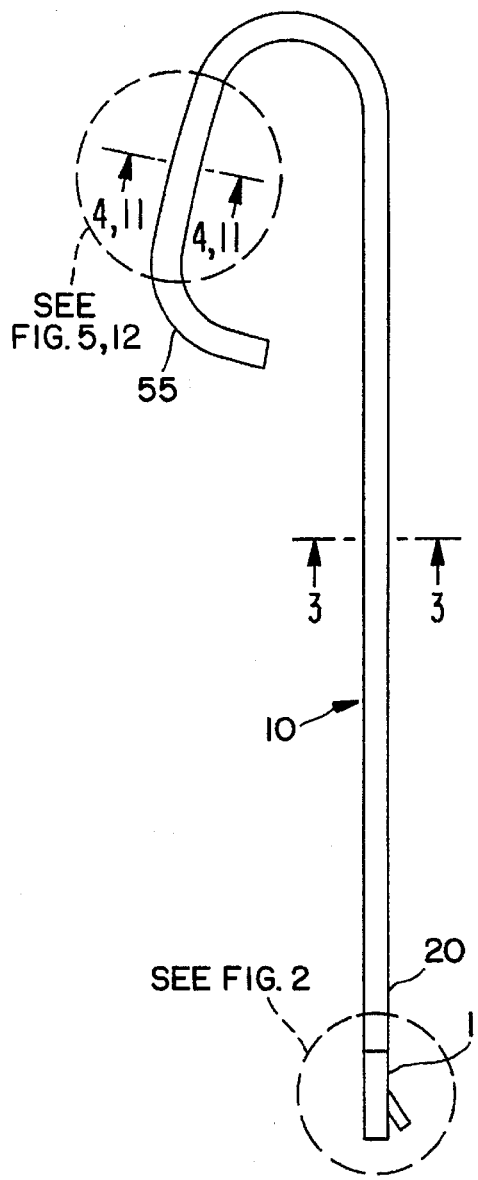
FIG. 1 is a plan view of the of the present invention.
Figure 2:
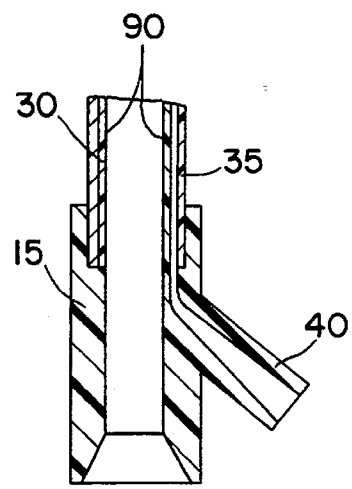
FIG. 2 is a blown-up cross-sectional view at Circle 2 of FIG. 1 showing the manifold attached to the proximal end of the present invention.
Figure 3:
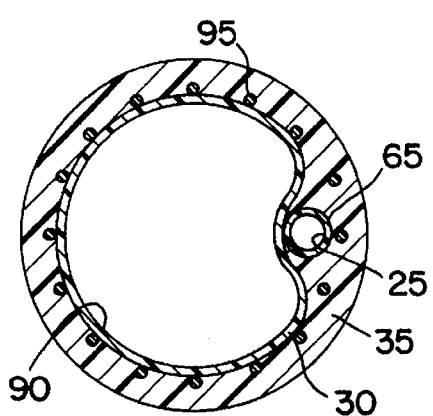
FIG. 3 is a transverse cross-sectional view taken at 3—3 of FIG. 1 showing the inner wall, intermediate torsional layer, outer wall and inflation lumen.
Figure 4:
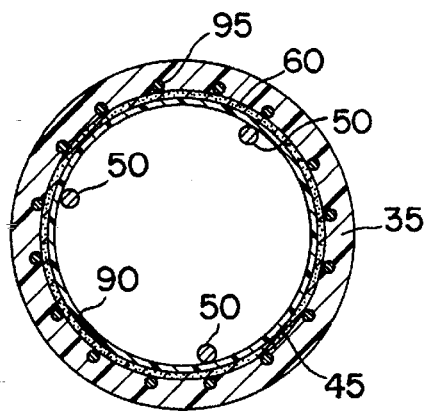
FIG. 4 is a transverse cross-sectional view taken at 4—4 of FIG. 1 showing the inflation bladder and stent inside the present invention.
Figure 5:
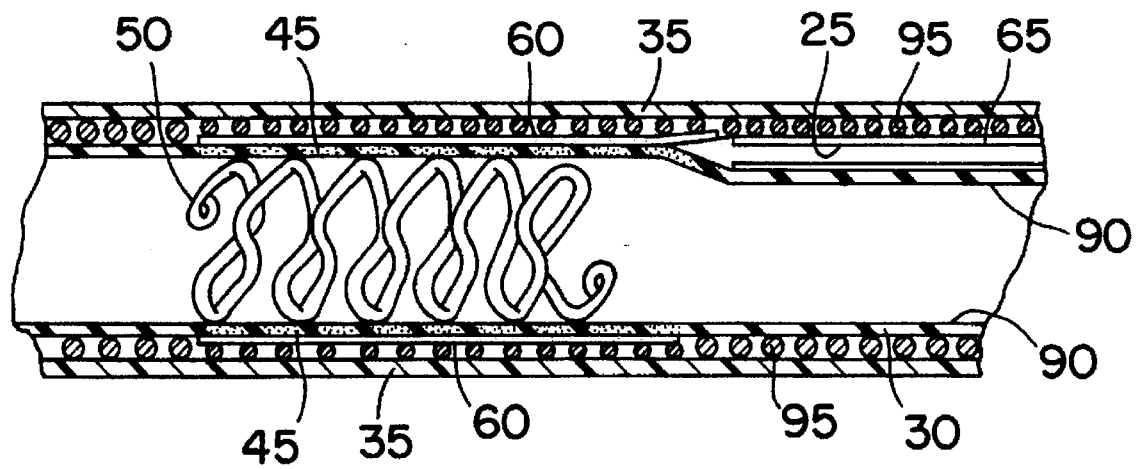
FIG. 5 is a blown-up longitudinal cross-sectional view of the guiding catheter at Circle 5 of FIG. 1 exposing the stent inside the present invention.

FIGS. 1–5 show the present invention of stent delivery guide catheter 10. The wall of the stent delivery guide catheter 10 is a multi-layered wall consisting of an inner wall 30, made of a flexible, lubricous material defining an inner lumen 90, an intermediate torsional layer 95 and an outer wall 35 that is made of a more rigid material. The difference in construction of the stent delivery guide catheter 10 and a conventional guide catheter is an area near the distal end 55, where a membrane 60 is inserted between the inner wall 30 and the intermediate torsional layer 95, creating an inflatable bladder 45. The stent delivery guide catheter 10 also has a manifold 15 affixed to the proximal end 20. A tube 65 is placed in the wall of the stent delivery guide catheter 10, between the inner wall 30 and the intermediate torsional layer 95 extends from the manifold 15 to the inflatable bladder 45, forming an inflation lumen 25. The inner wall 30 is made from PTFE, the intermediate torsional layer 95 is made from 0.002 inch diameter stainless steel wire braid, the outer wall 35 is made of polyurethane and the membrane 60 is made of a non-stick material. The tube 65 can be made of polyimide and has an inner diameter of 0.0125 inches and an outer diameter of 0.015 inches. An inflation device (not shown) can be connected to an inflation lumen 25 through inflation port 40 of the manifold 15. The inflation lumen 25 is in fluid communication with the inflatable bladder 45. The inflation lumen 25 thus provides a fluid path to the inflatable bladder 45 located adjacent to the distal end 55.

Figure 9:
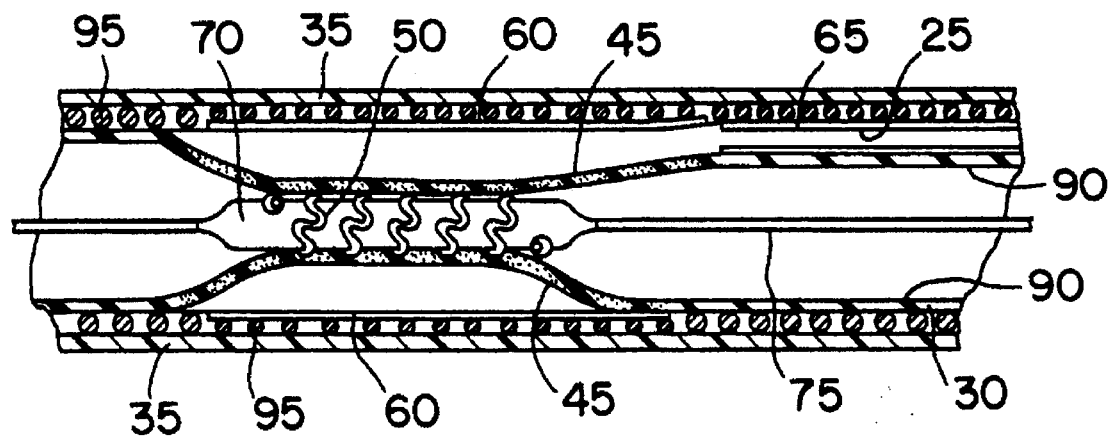
FIG. 9 is similar to FIG. 8 showing the bladder inflated, compressing the stent on the balloon.

The inflatable bladder 45 and a stent 50 are located at the distal end 55 of the stent delivery guide catheter 10. The inflatable bladder 45 is a collapsible segment of the inner wall 30 that is approximately 20 mm long but can vary depending on the length of the stent 50. Ideally the inflatable bladder 45 should be located in a relatively straight portion of the stent delivery guide catheter 10 near the distal end 55. To create the inflatable bladder 45, a membrane 60 is placed between the inner wall 30 and the intermediate torsional layer 95. The membrane 60 has non-stick properties that keep the inner wall 30 from adhering to the intermediate torsional layer 95 or the outer wall 35. The membrane 60 is 1–3 mils thick and can be made of Gortex™ material. When the inflatable bladder 45 is inflated, the sides expand and compress the stent 50 on to the balloon 70 of the dilatation catheter 75, as seen in FIG. 9.

Figure 11:
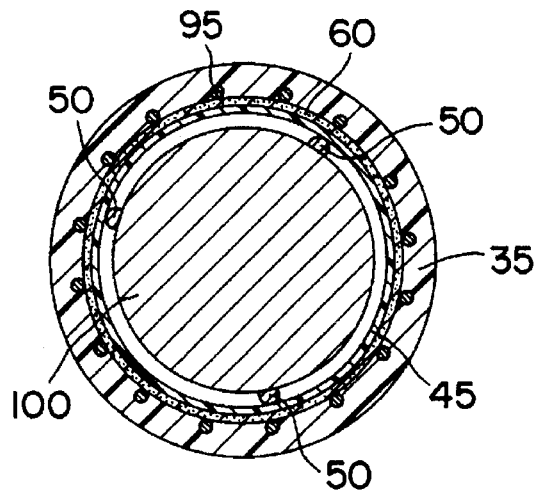
FIG. 11 is a transverse cross-sectional view taken at 11—11 of FIG. 1 showing the assembly mandrel inside the present invention.
Figure 12:
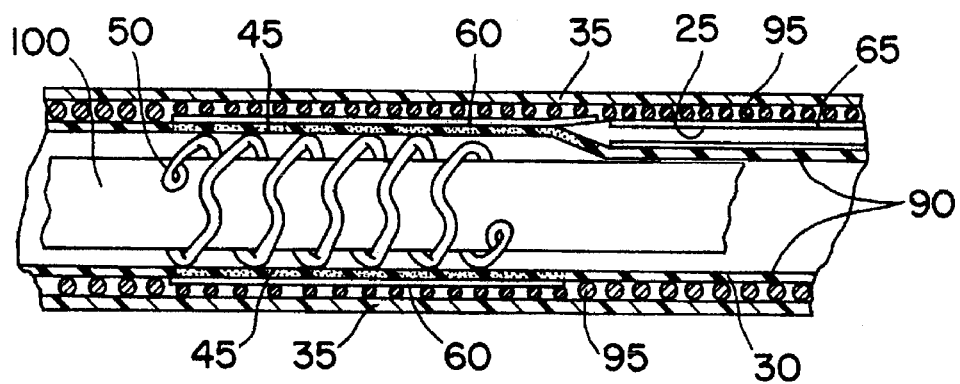
FIG. 12 is a blown-up longitudinal cross-sectional view of the guiding catheter at Circle 12 of FIG. 1 exposing the stent and the assembly mandrel inside the present invention.

For the fabrication of the stent delivery guide catheter 10, refer to FIGS. 11 & 12. These figures are for illustrative purposes only and are not to scale. The stent 50 is placed on the mandrel 100 in the desired location for the inflatable bladder 45. The inner wall 30 is then slid over both the mandrel 100 and the stent 50 to cover the stent 50. The inner wall 30 is masked off in the area of the inflatable bladder 45 and is then etched on its outer diameter to increase bonding strength with the subsequent layers. One type of etching material that could be used is Flouro Etch Safety Solvent manufactured by Action Technologies, Inc. the tube 65 is then positioned on top of the inner wall 30 to extend from the area of the inflatable bladder 45 to the inflation port 40 of the manifold 15. To create the inflatable bladder 45, a membrane 60, made of non-stick material, is positioned over the inner wall 30 and the distal end of the tube 65 in the area around the stent 50. The next layer, the intermediate torsional layer 95 made of stainless steel braid, is applied to cover the inner wall 30, the membrane 60 and the tube 65. The final layer applied is the outer wall 35, made of polyurethane which is used to bond all the layers together (except in the area of the membrane 60). The outer diameter of the stent delivery guide catheter 10 is approximately 0.104 inches and the inner diameter is approximately 0.079 inches, except in the area where the tube 65 is located, which will reduce the inner diameter slightly (see FIG. 3).

Figure 13:
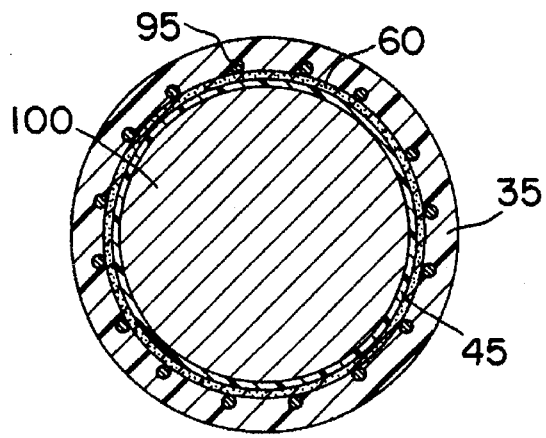
FIG. 13 is similar to FIG. 11 showing the assembly mandrel inside the present invention with the stent omitted.
Figure 14:
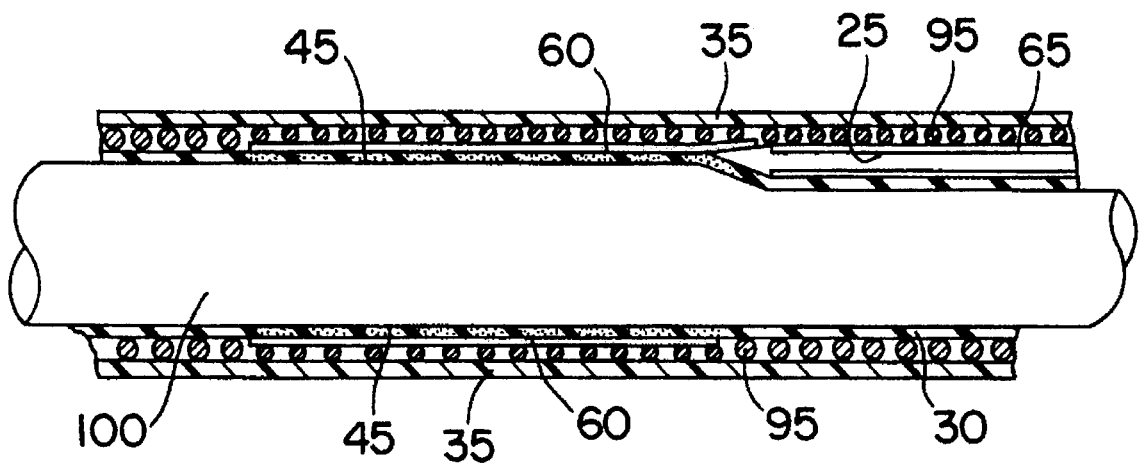
FIG. 14 is similar to FIG. 12 showing the assembly mandrel inside the present invention with the stent omitted.
Figure 18:
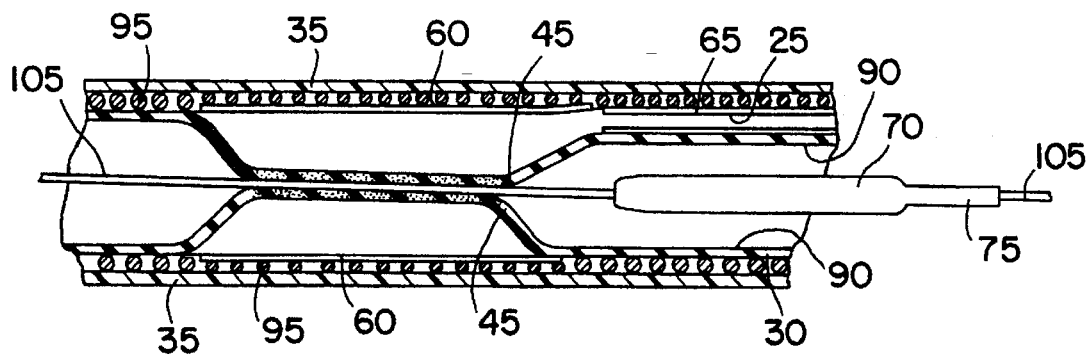
FIG. 18 shows the bladder inflated, compressing the guidewire.

A second method of fabrication may be envisioned in which the stent 50 is omitted in the above fabrication procedure, shown in FIGS. 13 & 14. This would create a guide catheter with an inflatable bladder that could be used for purposes other than stent delivery. For example, the inflatable bladder 45 could be used to facilitate exchanging the dilatation catheter 75 by inflating the bladder 45 and trapping the guidewire 105, as shown in FIG. 18.

Figure 6:
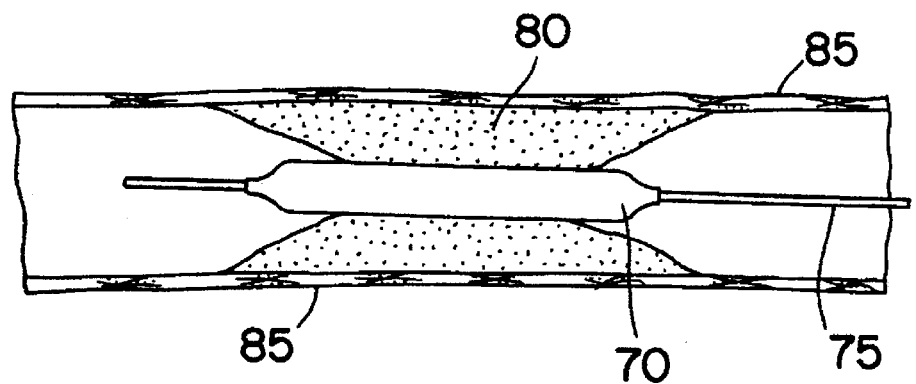
FIG. 6 shows a dilatation catheter and balloon inside a partially occluded
Figure 7:
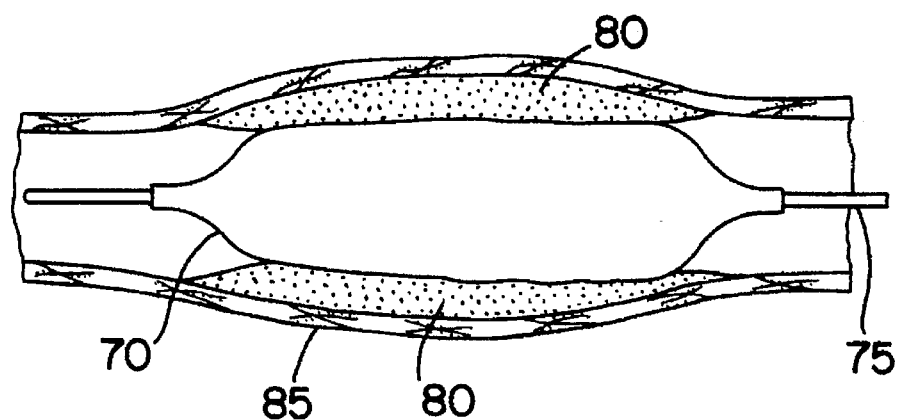
FIG. 7 is similar to FIG. 6 with the balloon inflated illustrating an angioplasty procedure.
Figure 8:
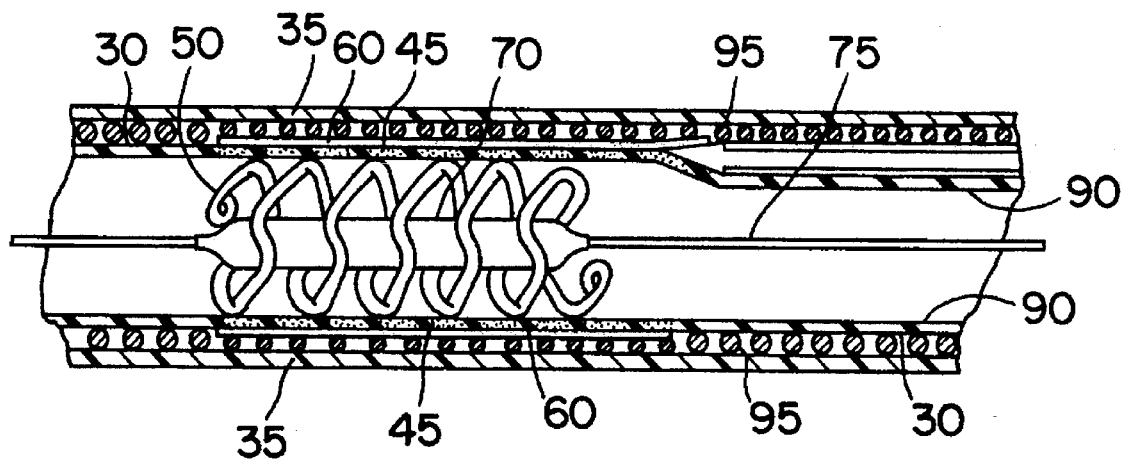
FIG. 8 is similar to FIG. 5 with the dilatation catheter balloon inside the present invention spanning the stent.
Figure 10:
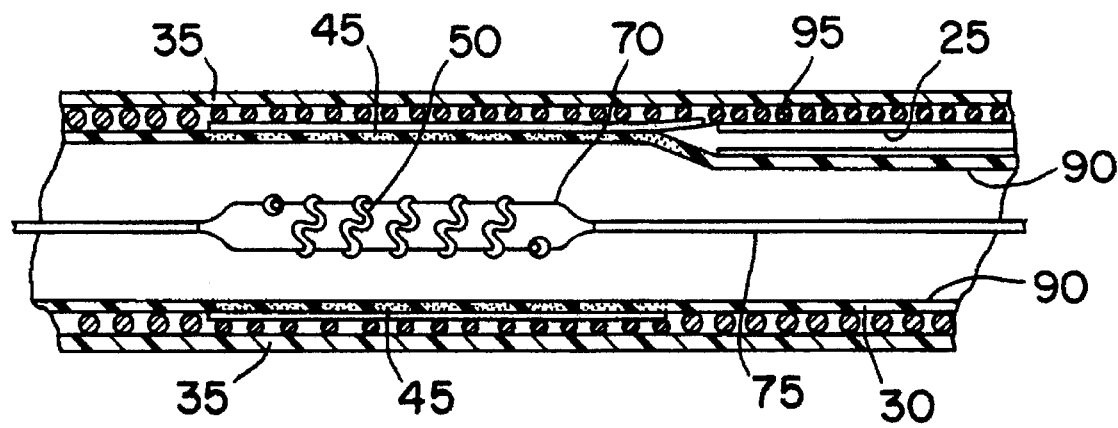
FIG. 10 is similar to FIG. 9 showing the bladder deflated and the stent mounted on the balloon of the dilatation catheter.

The method of using the invention as a stent delivery guide catheter 10 is as follows: FIGS. 6–10 show the method of use for the stent delivery guide catheter 10. At the beginning of a PTCA procedure, the stent delivery guide catheter 10 is inserted into the body. The dilatation catheter 75 is introduced through the inner lumen 90 of the stent delivery guide catheter 10 and advanced through the coronary artery 85 until the balloon 70 spans the stenosis 80, as shown in FIG. 6. The balloon 70 is then inflated to dilate the stenosis 80, as shown in FIG. 7. Once the stenosis 80 is dilated, the balloon 70 is deflated and pulled back into the inner lumen 90 of the stent delivery guide catheter 10 until the balloon 70 spans the stent 50 and the bladder 45, as shown in FIG. 8. FIG. 9 shows the stent 50 being mounted on the balloon 70. An inflation device (not shown) is attached to the manifold 15 and inflates the bladder 45. The walls of the inflatable bladder 45 expand and compress the stent 50 onto the balloon 70. Once the stent 50 is mounted on the balloon 70, the bladder 45 is deflated, as shown in FIG. 10. The dilatation catheter 75 is then advanced once again until the balloon 70, with stent 50, spans the now dilated stenosis 80 in the coronary artery 85. The balloon 70 is then inflated and the stent 50 is implanted into the stenosis 80. The balloon 70 is deflated and removed leaving the stent 50 to keep the artery 85 open.

Figure 15:
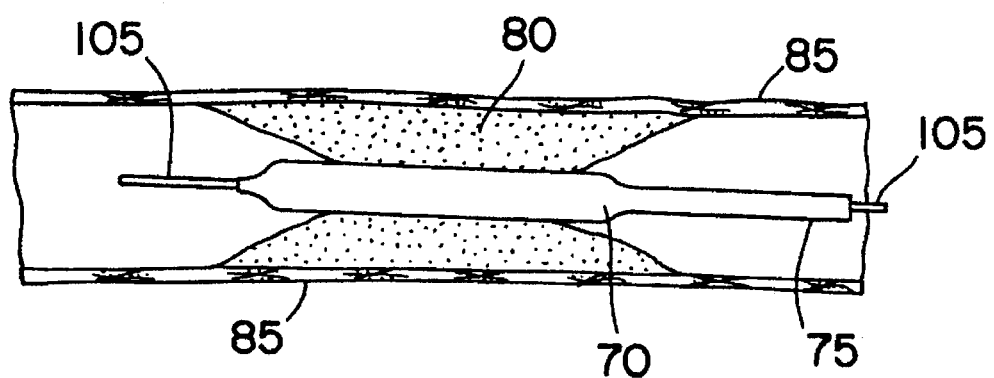
FIG. 15 is similar to FIG. 6 showing an over-the-wire dilatation catheter, balloon and guidewire inside a partially occluded artery.
Figure 16:
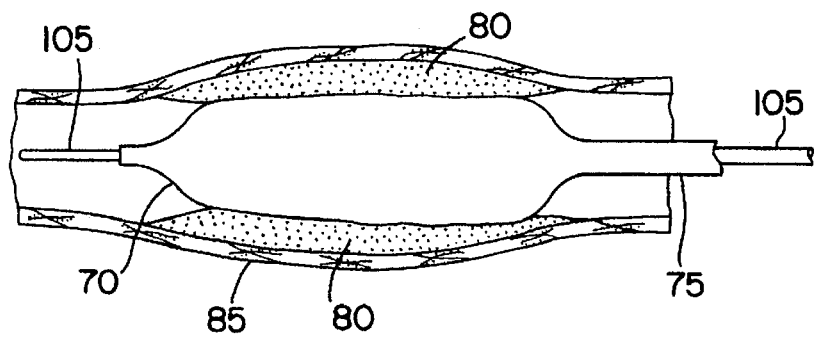
FIG. 16 is similar to FIG. 7 showing an over-the-wire dilatation catheter balloon inflated illustrating an angioplasty procedure.
Figure 17:
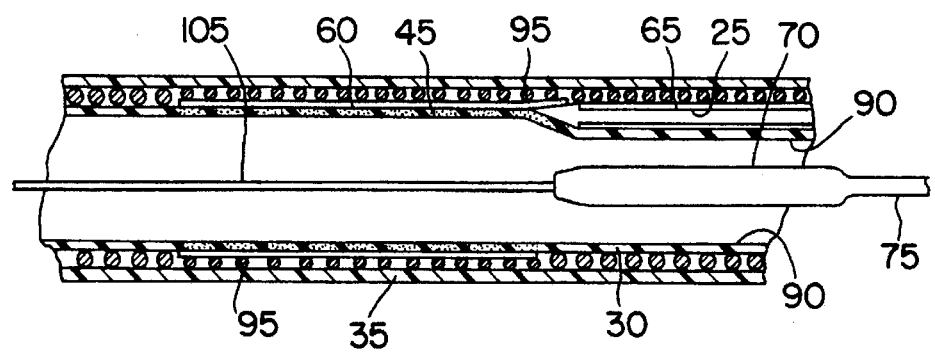
FIG. 17 shows the over-the-wire dilatation catheter and guidewire inside the present invention.

The method of using the invention as a catheter exchange system is as follows: FIGS. 15–18 show the method of using the stent delivery guide catheter 10 to aid the exchange of the dilatation catheter 75. For this method, the stent delivery guide catheter 10 is used without the stent 50, either the stent 50 is crimped on the dilatation catheter 75 prior to this method of use or the stent 50 was omitted during fabrication of the stent delivery guide catheter 10. For use with this method, the dilatation catheter 75 is an over-the-wire catheter used in conjunction with a guidewire 105. At the beginning of a PTCA procedure, the stent delivery guide catheter 10 is inserted into the body. The dilatation catheter 75 and the guidewire 105 are introduced through the inner lumen 90 of the stent delivery guide catheter 10 and advanced through the coronary artery 85 until the balloon 70 spans the stenosis 80, as shown in FIG. 15. The balloon 70 is then inflated to dilate the stenosis 80, as shown in FIG. 16. Once the stenosis 80 is dilated, the doctor may want to exchange the dilatation catheter 75 for one of a different size or type. While holding the guidewire 105 in position across the stenosis 80, the dilatation catheter 75 is pulled proximally into the inner lumen 90 of the stent delivery guide catheter 10 until the balloon 70 is proximal of the bladder 45, as shown in FIG. 17. An inflation device (not shown) is attached to the manifold 15 and inflates the bladder 45. The walls of the inflatable bladder 45 inflate and compress the guidewire 105, holding it in place across the stenosis 80. The dilatation catheter 75 can now be pulled out of the stent delivery guide catheter 10. The next size or type of dilatation catheter 75 desired is then advanced over the guidewire 105 until it meets the inflatable bladder 45. The inflatable bladder 45 is then deflated and the dilatation catheter 75 is advanced over the guidewire 105 to the stenosis 80.

Although a particular embodiment oft he invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention.

| No. | Component |
| --- | --- |
| 10 | Stent Delivery Guide Catheter |
| 15 | Manifold |
| 20 | Proximal end |
| 25 | Inflation Lumen |
| 30 | Inner Wall |
| 35 | Outer Wall |
| 40 | Inflation Port |
| 45 | Bladder |
| 50 | Stent |
| 55 | Distal End |
| 60 | Membrane |
| 65 | Tube |
| 70 | Balloon |
| 75 | Dilatation Catheter |
| 80 | Stenosis |
| 85 | Artery |
| 90 | Inner Lumen |
| 95 | Intermediate Torsional Layer |
| 100 | Mandrel |
| 105 | Guidewire |

What is claimed is:

1. A stent delivery guide catheter comprising:

a guide catheter body having proximal and distal ends with a cylindrical outer wall and a coaxially bonded inner wall defining an inner lumen;

radially non-self expandable and compressibly crimpable stent located inside the guide catheter body that is coaxial with and removably attached to the inner wall; and means for compressing the stent radially inward, wherein the means for compressing the stent is an inflatable means connected to a tube disposed between the coaxially bonded inner wall and the outer wall, the tube defining an inflation lumen providing fluid communication between the inflatable means and an inflation port located at the proximal end of the guide catheter body.

2. A stent delivery guide catheter in accordance with claim 1, wherein the inflatable means is an area of the inner wall comprising a membrane with non-stick properties, the membrane being disposed of between the inner wall and the outer wall and forming an inflatable bladder in fluid communication with the inflation lumen.

3. A stent delivery guide catheter in accordance with claim 2, wherein the membrane with non-stick properties is made of expanded polytetrafluoroethylene.

4. A stent delivery guide catheter in accordance with claim 1 having an intermediate torsional layer coaxially bonded between the coaxially bonded inner wall and the outer wall.

5. A stent delivery guide catheter in accordance with claim 4, wherein the intermediate torsional layer is made of stainless steel braid.

6. A stent delivery guide catheter in accordance with claim 1, wherein the outer wall is made of polyurethane.

7. A stent delivery guide catheter comprising:

a guide catheter body having proximal and distal ends with a cylindrical outer wall and a coaxially bonded inner wall defining an inner lumen, an intermediate torsional layer coaxially bonded between the coaxially bonded inner wall and the outer wall;

a radially non-self expandable and compressibly crimpable stent located inside the guide catheter body that is coaxial with and removably attached to the inner wall; and a means for compressing the stent radially inward, wherein the means for compressing the stent is an inflatable means connected to a tube disposed between the coaxially bonded inner wall and the intermediate torsional layer, the tube defining and inflation lumen providing fluid communication between the inflatable means and an inflation port located at the proximal end of the guide catheter body.

8. A stent delivery guide catheter in accordance with claim 7, wherein the inflatable means is an area of the inner wall comprising a membrane with non-stick properties, the membrane being disposed between the inner wall and the intermediate torsional layer and forming an inflatable bladder in fluid communication with the inflation lumen.

9. A stent delivery guide catheter comprising:

a guide catheter body having proximal and distal ends with a cylindrical outer wall and a coaxially bonded inner wall, the inner wall defining and inner lumen;

a membrane with non-stick properties disposed between and coaxial with the inner wall and outer wall, the membrane forming an inflatable bladder having an inner diameter; a tube disposed between the coaxially bonded inner wall and the outer wall, the tube defining an inflation lumen and providing fluid communication between the inflatable bladder and an inflation port, and a radially non-self expandable and compressibly crimpable stent having an inner and outer diameter, the outer diameter being frictionally engaged with the inner diameter of the inflatable bladder.

10. A stent delivery guide catheter in accordance with claim 9, wherein the outer wall is made of polyurethane.

11. A stent delivery guide catheter in accordance with claim 9, wherein the tube is made of polyimide.

12. A stent delivery guide catheter in accordance with claim 9, wherein the membrane with non-stick properties is made of expanded polytetrafluoroethylene.

13. A guide catheter used for catheter exchange comprising:

a guide catheter body having proximal and distal ends with a cylindrical outer wall, a coaxially bonded intermediate torsional layer and a coaxially bonded inner wall defining an inner lumen; and an inflatable means connected to a tube disposed between the coaxially bonded inner wall and the intermediate torsional layer, the tube defining an inflation lumen providing fluid communication between the inflatable means and an inflation port located at the proximal end of the guide catheter body.

14. A guide catheter in accordance with claim 13, wherein the outer wall is made of polyurethane.

15. A guide catheter in accordance with claim 13, wherein the intermediate torsional layer is made of stainless steel braid.

16. A guide catheter in accordance with claim 13, wherein the inflatable means is an area of the inner wall having a membrane with non-stick properties disposed between the inner wall and the intermediate torsional layer, the membrane forming an inflatable bladder having fluid communication with the inflation lumen.

17. A guide catheter in accordance with claim 16, wherein the membrane with non-stick properties is made of expanded polytetrafluoroethylene.

18. A guide catheter used for catheter exchange comprising:

a guide catheter body having proximal and distal ends with a cylindrical outer wall, a coaxially bonded intermediate torsional layer and a coaxially bonded inner wall defining an inner lumen;

a membrane with non-stick properties disposed coaxially between the inner wall and the intermediate torsional layer, the membrane forming an inflatable bladder; and a tube disposed between the coaxially bonded inner wall and the intermediate torsional layer defining an inflation lumen, the tube providing fluid communication between the inflatable bladder and an inflation port located at the proximal end of the guide catheter body.

19. A guide catheter in accordance with claim 18, wherein the outer wall is made of polyurethane.

20. A guide catheter in accordance with claim 18, wherein the tube is made of polyimide.

21. A guide catheter in accordance with claim 18, wherein the membrane with on-stick properties is made of expanded polytetrafluoroethylene.

22. A method of manufacturing a stent delivery guide catheter comprising the steps of:

(a) providing a mandrel with proximal and distal ends;

(b) providing an inflation port;

(c) locating the inflation port near the proximal end of the mandrel;

(d) providing a radially expandable and compressible stent;

(e) sliding the stent over the mandrel;

(f) advancing a flexible inner wall layer over the stent and mandrel;

(g) placing a membrane with non stick properties over the inner wall layer and covering the area of the stent;

(h) etching the inner wall proximal and distal to the membrane;

(i) disposing a tube over the inner wall from the proximal end of the membrane to the inflation port, the tube defining an inflation lumen;

(j) applying polyurethane over the tube, the membrane and the inner wall layer to form a cylindrical outer wall;

(k) removing the mandrel; and (l) forming an inflatable bladder in the area of the membrane, the inflatable bladder being located between the membrane and the inner wall, the inflatable bladder being in fluid communication with the inflation lumen and the inflation port.

23. A method of manufacturing a guide catheter with an inflatable bladder comprising the steps of:

(a) providing a mandrel with proximal and distal ends;

(b) providing an inflation port;

(c) locating the inflation near the proximal end of the mandrel;

(d) advancing a flexible inner wall layer over the mandrel;

(e) placing a membrane with non stick properties over the inner wall layer near the distal end of the mandrel;

(f) etching the inner wall proximal and distal to the membrane;

(g) disposing a tube over the inner wall from the proximal end of the membrane to the inflation port, the tube defining an inflation lumen;

(h) covering the tube, the membrane and the inner wall with an intermediate torsional layer;

(i) applying polyurethane over the intermediate torsional layer to form a cylindrical outer wall;

(j) removing the mandrel; and (k) forming an inflatable bladder in the area of the membrane between the membrane and inner wall, the inflatable bladder being in fluid communication with the inflation lumen and inflation port.

24. A stent delivery guide catheter comprising:

a guide catheter body having proximal and distal ends with a cylindrical outer wall and a coaxially bonded inner wall, the inner wall defining an inner lumen, the outer wall is made of rigid material and the inner wall is made of flexible material;

a membrane with non-stick properties disposed coaxially between with the inner wall and outer wall, the membrane forming an inflatable bladder between the inner wall and outer wall, the inflatable bladder having an inner diameter;

a tube disposed between the coaxially bonded inner wall and the outer wall, the tube defining an inflation lumen and providing fluid communication between the inflatable bladder and an inflation port located at the proximal end of the guide catheter body; and a radially non-self expandable and compressibly crimpable stent made of malleable metal that plastically deforms upon applied stress, the stent having an inner and outer diameter, the outer diameter being removably attached with the inner diameter of the inflatable bladder.

25. A stent delivery guide catheter comprising:

a guide catheter body having proximal and distal ends with a cylindrical outer wall, a coaxially bonded intermediate torsional layer and a coaxially bonded inner wall defining an inner lumen, the outer wall is made of rigid material, the intermediate torsional layer is made of a woven material and the inner wall is made of flexible material;

a membrane with non-stick properties disposed coaxially between the inner wall and the intermediate torsional layer, the membrane forming an inflatable bladder;

a tube disposed between the coaxially bonded inner wall and the intermediate torsional layer defining an inflation lumen, the tube providing fluid communication between the inflatable bladder and an inflation port located at the proximal end of the guide catheter body; and a radially non-self expandable and compressibly crimpable stent made of malleable metal that plastically deforms upon applied stress, the stent is located inside the guide catheter body and is coaxial with and removably attached to the inner wall adjacent to the inflatable bladder such that introduction of fluid into the inflatable bladder compresses the stent radially inward.

* * * * *

UNITED STATES PATENT AND TRADEMARK OFFICE
CERTIFICATE OF CORRECTION

PATENT NO. : 5,628,754
DATED : May 13, 1997
INVENTOR(S) : Shevlin, et. al.

It is certified that error appears in the above-indentified patent and that said Letters Patent is hereby corrected as shown below:

Item [75],
Title Page Inventors List: "Paul W. Krejol" should be "Paul W. Krejci"

Col. 6, Line 37, "means for" should be "a means for"
Col. 7, Line 9, "defining and" should be "defining an"
Col. 7, Line 22, "defining and" should be "defining an"
Col. 7, Line 29, "port" should be "port;"
Col. 8, Line 21, "on-stick" should be "non stick"
Col. 8, Line 55, "inflation" should be "inflation port"
Col. 9, Line 15, "with the" should be "the"
Col. 2, Line 2, "position" should be "positioned"
Col. 3, Line 30, "occluded" should be "occluded artery;"
Col. 3, Line 65, "of on a stent" should be "of a stent"
Col. 4, Line 11, "extends" should be "and extends"
Col. 4, Line 50, "the tube" should be "The tube"
Col. 4, Line 55, "wail 30" should be "wall 30"

Signed and Sealed this

Twenty-first Day of October 1997

Attest:

BRUCE LEHMAN

Attesting Officer

Commissioner of Patents and Trademarks